(12) United States Patent
Zador et al.

(10) Patent No.: US 9,752,179 B2
(45) Date of Patent: Sep. 5, 2017

(54) TRANS-SPLICING TRANSCRIPTOME PROFILING

(71) Applicants: Anthony M. Zador, Cold Spring Harbor, NY (US); Ian D. Peikon, Cold Spring Harbor, NY (US); Petr Znamenskiy, Basel (CH)

(72) Inventors: Anthony M. Zador, Cold Spring Harbor, NY (US); Ian D. Peikon, Cold Spring Harbor, NY (US); Petr Znamenskiy, Basel (CH)

(73) Assignee: COLD SPRING HARBOR LABORATORY, Cold Spring Harbor, NY (US)

(*) Notice: Subject to any disclaimer, the term of this patent is extended or adjusted under 35 U.S.C. 154(b) by 559 days.

(21) Appl. No.: 14/208,446

(22) Filed: Mar. 13, 2014

(65) Prior Publication Data
US 2014/0272988 A1    Sep. 18, 2014

Related U.S. Application Data

(60) Provisional application No. 61/782,389, filed on Mar. 14, 2013.

(51) Int. Cl.
C12Q 1/68    (2006.01)
(52) U.S. Cl.
CPC .................. C12Q 1/6809 (2013.01)
(58) Field of Classification Search
None
See application file for complete search history.

(56) References Cited

U.S. PATENT DOCUMENTS

| 8,003,381 B2 | 8/2011 | Klimyuk et al. |
| 9,447,411 B2* | 9/2016 | Chenchik ............ C12N 15/1072 |
| 2012/0245039 A1* | 9/2012 | Roth .................... C12Q 1/6874 506/2 |
| 2014/0283156 A1 | 9/2014 | Zador et al. |

OTHER PUBLICATIONS

Kohler et al. (1999) Trans-splicing Ribozymes for Targeted Gene Delivery, *J. Mol. Biol.* 285:1935-1950.
Zador et al. (2012) Sequencing the Connectome, *PLoS Biology* 10(10):e1001411.

* cited by examiner

*Primary Examiner* — Samuel Woolwine
(74) *Attorney, Agent, or Firm* — Gary J. Gershik; Cooper & Dunham LLP

(57) ABSTRACT

The present invention provides a method of identifying mRNA transcripts in the transcriptome of a cell comprising i) delivering into the cell a donor expression vector comprising nucleotides in a sequence encoding a trans-splicing barcode cassette, ii) exposing the cell to conditions such that the cell produces multiple copies of the trans-splicing barcode cassette encoded by the donor expression vector, which multiple copies of the trans-splicing barcode cassette each splice the barcode polynucleotide onto a mRNA transcript of the cell, thereby forming multiple mRNA transcripts of the cell, each spliced to the barcode polynucleotide; and iii) identifying the multiple mRNA transcripts that are spliced to the barcode polynucleotides, thereby identifying mRNA transcripts in the transcriptome of the cell.

24 Claims, 9 Drawing Sheets

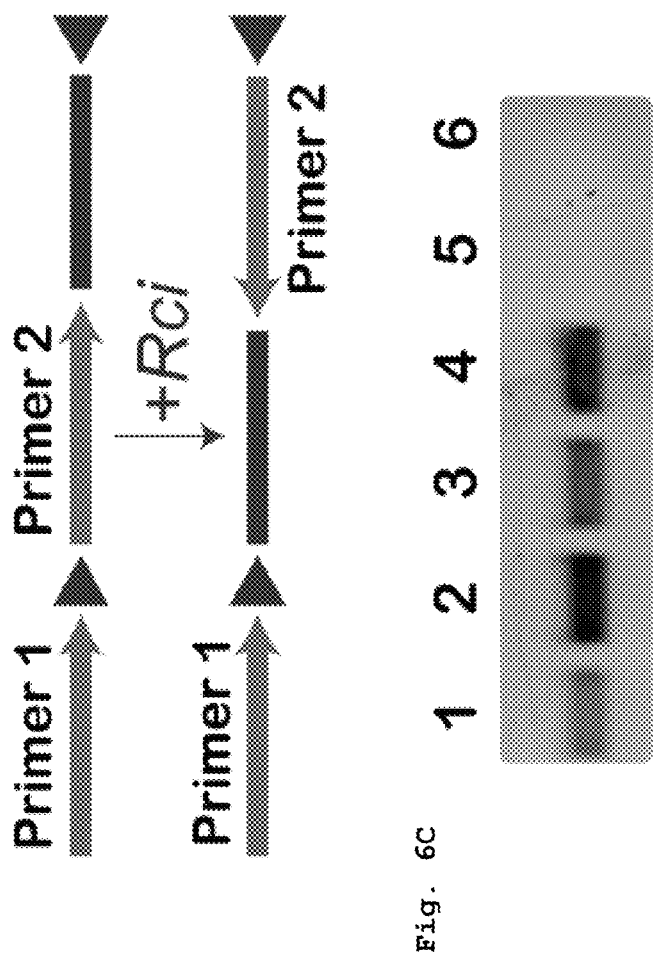
Fig. 6B
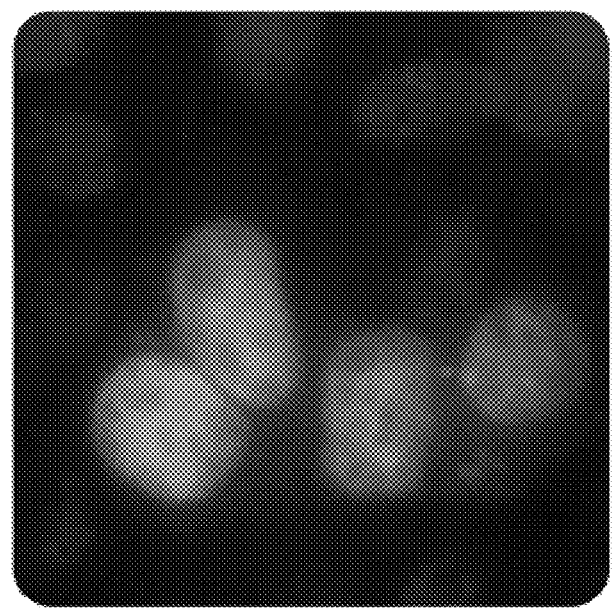
Fig. 6C
Fig. 6A

TRANS-SPLICING TRANSCRIPTOME PROFILING

This application claims priority of U.S. Provisional Patent Application No. 61/782,389, filed Mar. 14, 2013, the entire contents of which are hereby incorporated herein by reference.

This application incorporates-by-reference nucleotide and/or amino acid sequences which are present in the file named "140313_5981_84813_Sequence_Listing_REB.txt," which is 0.47 kilobytes in size, and which was created Mar. 13, 2014 in the IBM-PC machine format, having an operating system compatibility with MS-windows, which is contained in the text file filed Mar. 13, 2014 as part of this application.

Throughout this application, various publications are referenced, including referenced in parenthesis. Full citations for publications referenced in parenthesis may be found listed at the end of the specification immediately preceding the claims. The disclosures of all referenced publications in their entireties are hereby incorporated by reference into this application in order to more fully describe the state of the art to which this invention pertains.

BACKGROUND OF THE INVENTION

Heterogeneity plays an important role in the proper and abnormal functioning of many biological systems from neural computation to tumor development. Methods of probing heterogeneity in cellular expression have been limited by technical challenges (i.e. sorting and separating individual cells, isolation of sufficient quantity and quality RNA from individual cells, etc).

A method for rapidly profiling the transcriptomes of multiple cells, while retaining identities of individual cells would be a major advance and is needed.

SUMMARY OF THE INVENTION

The present invention provides a method of identifying mRNA transcripts in the transcriptomes of multiple cells within a population of cells comprising
  i) delivering into each of at least two cells a donor expression vector comprising nucleotides in a sequence encoding a trans-splicing barcode cassette, wherein the trans-splicing barcode cassette comprises
    a) a first portion, the nucleotide sequence of which encodes an intron comprising as part of its 3' end, or followed at its 3' end by a splice-site nucleotide sequence;
    followed at its 3' end by,
    b) a second portion, the nucleotide sequence of which encodes a barcode polynucleotide;
    followed at its 3' end by
    c) a third portion, which encodes a nucleotide identification element sequence,
  ii) exposing the cell to conditions such that each of the at least two cells produces multiple copies of the trans-splicing barcode cassette encoded by the donor expression vector, which multiple copies of the trans-splicing barcode cassette each splice the barcode polynucleotide onto a mRNA transcript of the at least two cells, thereby forming multiple spliced mRNA transcripts of the cell, each spliced to the barcode polynucleotide; and
  iii) identifying the multiple mRNA transcripts that are spliced to the barcode polynucleotides, thereby identifying mRNA transcripts in the transcriptomes of multiple cells within a population of cells.

The present invention provides a method of identifying mRNA transcripts in the transcriptome of a cell comprising
  i) delivering into the cell a donor expression vector comprising nucleotides in a sequence encoding a trans-splicing barcode cassette, wherein the trans-splicing barcode cassette comprises
    a) a first portion, the nucleotide sequence of which encodes an intron comprising as part of its 3' end, or followed at its 3' end by a splice-site nucleotide sequence;
    followed at its 3' end by,
    b) a second portion, the nucleotide sequence of which encodes a barcode polynucleotide;
    followed at its 3' end by
    c) a third portion, which encodes a nucleotide identification element sequence,
  ii) exposing the cell to conditions such that the cell produces multiple copies of the trans-splicing barcode cassette encoded by the donor expression vector, which multiple copies of the trans-splicing barcode cassette each splice the barcode polynucleotide onto a mRNA transcript of the cell, thereby forming multiple mRNA transcripts of the cell, each spliced to the barcode polynucleotide; and
  iii) identifying the multiple mRNA transcripts that are spliced to the barcode polynucleotides, thereby identifying mRNA transcripts in the transcriptome of the cell.

DETAILED DESCRIPTION OF THE INVENTION

Figure 1:
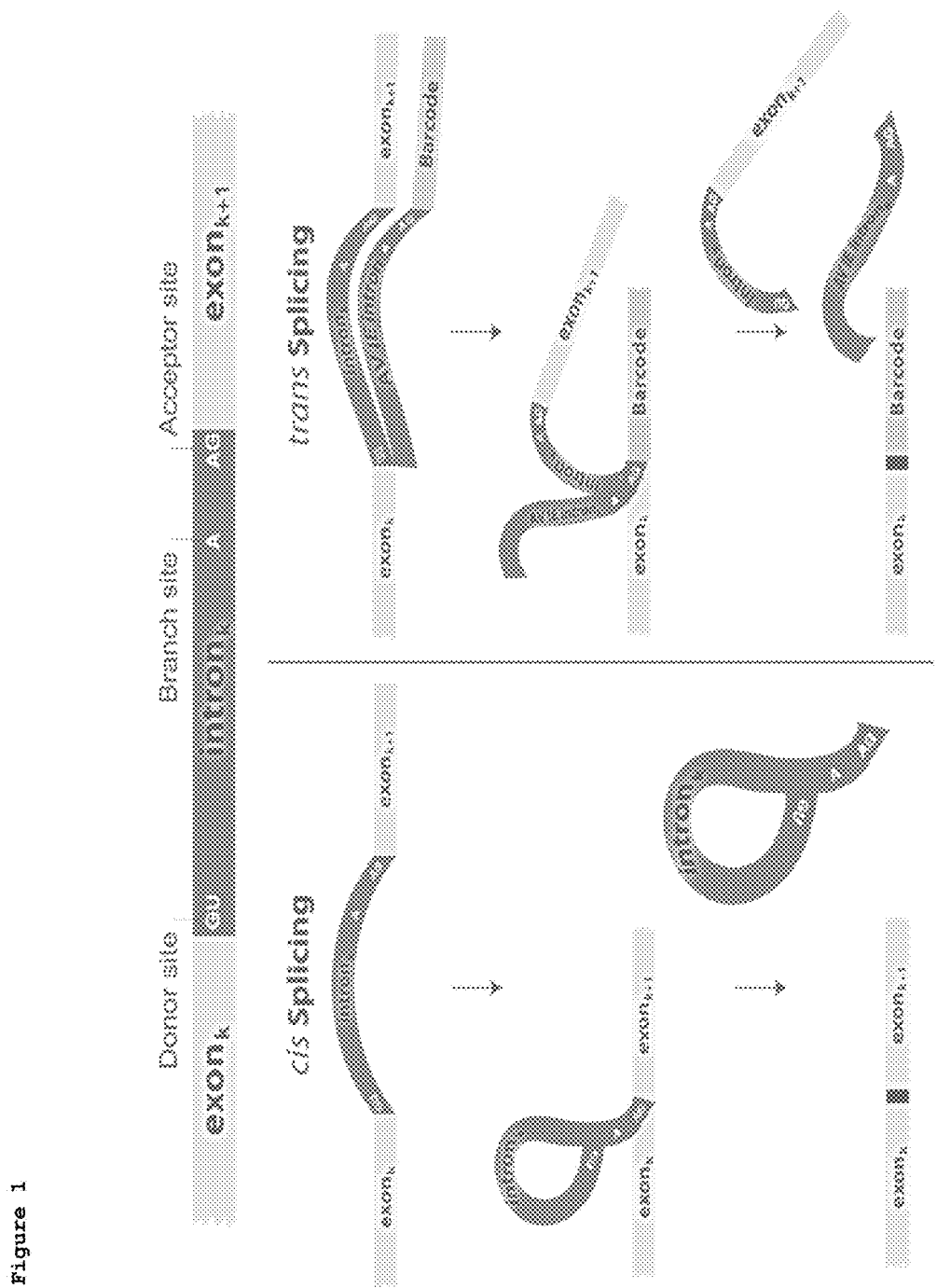
FIG. 1. The promiscuous trans-splicing barcode cassette is designed to mimic an intron-3' exon by using sequence elements from the Adeno Virus Immediate Early Intron. Overexpression of the cassette.

The present invention provides a method of identifying mRNA transcripts in the transcriptomes of multiple cells within a population of cells comprising
  i) delivering into each of at least two cells a donor expression vector comprising nucleotides in a sequence encoding a trans-splicing barcode cassette, wherein the trans-splicing barcode cassette comprises
    a) a first portion, the nucleotide sequence of which encodes an intron comprising as part of its 3' end, or followed at its 3' end by a splice-site nucleotide sequence;
    followed at its 3' end by,
    b) a second portion, the nucleotide sequence of which encodes a barcode polynucleotide;
    followed at its 3' end by
    c) a third portion, which encodes a nucleotide identification element sequence,
  ii) exposing the cell to conditions such that each of the at least two cells produces multiple copies of the trans-splicing barcode cassette encoded by the donor expression vector, which multiple copies of the trans-splicing barcode cassette each splice the barcode polynucleotide onto a mRNA transcript of the at least two cells, thereby forming multiple spliced mRNA transcripts of the cell, each spliced to the barcode polynucleotide; and
  iii) identifying the multiple mRNA transcripts that are spliced to the barcode polynucleotides, thereby identifying mRNA transcripts in the transcriptomes of multiple cells within a population of cells.

In some embodiments, the intron comprises the Adeno Virus immediate early intron.

In some embodiments, the intron is the Adeno Virus immediate early intron.

In some embodiments, the Adeno Virus immediate early intron is followed at its 3' end by the splice-site nucleotide sequence.

In some embodiments, the splice-site nucleotide sequence is CAG.

In some embodiments, the intron is other than the Adeno Virus immediate early intron.

In some embodiments, in step iii) the nucleotide identification element sequence is used to identify the multiple mRNA transcripts that are spliced to the barcode polynucleotide.

In some embodiments, the nucleotide identification element sequence comprises a nucleotide sequence which is used to identify the multiple mRNA transcripts that are spliced to the barcode polynucleotides.

In some embodiments, the nucleotide identification element sequence comprises a nucleotide sequence which is used to reverse transcribe the barcode polynucleotide and at least a portion of the multiple mRNA transcripts that are spliced to the barcode polynucleotide.

In some embodiments, the nucleotide identification element sequence comprises a nucleotide sequence which is used to sequence the barcode polynucleotide and at least a portion of the multiple mRNA transcripts that are spliced to the barcode polynucleotide.

In some embodiments, the population of cells is an in vitro culture of cells.

In some embodiments, the population of cells is within the tissue obtained from or present within an organism.

In some embodiments, each donor expression vector is delivered by a recombinant virus.

In some embodiments, each donor expression vector is delivered by transfection.

In some embodiments, each donor expression vector comprises nucleotides in a sequence encoding a trans-splicing barcode cassette with a barcode polynucleotide having a nucleotide sequence that is different from the barcode polynucleotide sequence of the trans-splicing barcode cassette encoded by any other donor expression vector, such that each of the at least two cells within the population of cells expresses a trans-splicing barcode cassette having a unique barcode polynucleotide sequence.

In some embodiments, the nucleotide sequence of each unique barcode nucleotide sequence is from a high-diversity barcode library.

In some embodiments, the high-diversity barcode library is generated by shotgun cloning of oligonucleotides.

In some embodiments, the nucleotide sequence of each unique barcode polynucleotide is static.

In some embodiments, each donor expression vector comprises nucleotides in a sequence encoding a trans-splicing barcode cassette having the same nucleotide sequence, wherein the portion of the nucleotide sequence of the expression vector that encodes the barcode nucleotide sequence is altered within the at least two cells, such that each of the at least two cells within the population expresses copies of the trans-splicing barcode cassette having a unique barcode polynucleotide sequence.

In some embodiments, a recombinase alters the nucleotide sequence of the expression vector that encodes the barcode nucleotide sequence.

In some embodiments, the recombinase is expressed in each cell into which a trans-splicing barcode cassette is delivered.

In some embodiments, each donor expression vector further comprises nucleotides in a sequence encoding the recombinase.

In some embodiments, a second expression vector comprising nucleotides in a sequence encoding the recombinase is delivered into the at least two cells concurrently with the donor expression vector.

In some embodiments, the barcode polynucleotide comprises multiple unique DNA segments of multiple nucleotides separated by recombination sites, such that the multiple unique DNA segments are recombined by the recombinase when the recombinase is co-expressed with the donor expression vector in each of the at least two cells.

In some embodiments, the barcode polynucleotide sequence comprises at least 2, 3, 4, 5, 6, 7, 8, 9, 10, 11, 12, 13, 14 or 15 unique DNA segments.

In some embodiments, each unique DNA segment comprises 1-200 nucleotides.

In some embodiments, the recombinase is Rci, and the recombination sites are each a pair of sfx recombination sites.

In some embodiments, the sfx recombination sites within each pair of sfx recombination sites are in an opposing orientation to each other.

In some embodiments, the recombinase is Cre, and the recombination sites are loxP sites.

In some embodiments, the recombinase is Flp, and the recombination sites are FRT sites.

In some embodiments, the recombinase is PhiC31, and the recombination sites are att sites.

The present invention provides a method of identifying mRNA transcripts in the transcriptome of a cell comprising
i) delivering into the cell a donor expression vector comprising nucleotides in a sequence encoding a trans-splicing barcode cassette, wherein the trans-splicing barcode cassette comprises
  a) a first portion, the nucleotide sequence of which encodes an intron comprising as part of its 3' end, or followed at its 3' end by a splice-site nucleotide sequence;
  followed at its 3' end by,
  b) a second portion, the nucleotide sequence of which encodes a barcode polynucleotide;
  followed at its 3' end by
  c) a third portion, which encodes a nucleotide identification element sequence,
ii) exposing the cell to conditions such that the cell produces multiple copies of the trans-splicing barcode cassette encoded by the donor expression vector, which multiple copies of the trans-splicing barcode cassette each splice the barcode polynucleotide onto a mRNA transcript of the cell, thereby forming multiple mRNA transcripts of the cell, each spliced to the barcode polynucleotide; and
iii) identifying the multiple mRNA transcripts that are spliced to the barcode polynucleotides, thereby identifying mRNA transcripts in the transcriptome of the cell.

In some embodiments, the intron comprises the Adeno Virus immediate early intron.

In some embodiments, the intron is the Adeno Virus immediate early intron.

In some embodiments, the Adeno Virus immediate early intron is followed at its 3' end by the splice-site nucleotide sequence.

In some embodiments, the splice-site nucleotide sequence is CAG.

In some embodiments, the intron is other than the Adeno Virus immediate early intron.

In some embodiments, in step iii) the nucleotide identification element sequence is used to identify the multiple mRNA transcripts that are spliced to the barcode polynucleotide.

In some embodiments, the nucleotide identification element sequence comprises a nucleotide sequence which is used to identify the multiple mRNA transcripts that are spliced to the barcode polynucleotide.

In some embodiments, the nucleotide identification element sequence comprises a nucleotide sequence which is used to reverse transcribe the barcode polynucleotide and at least a portion of the multiple mRNA transcripts that are spliced to the barcode polynucleotide.

In some embodiments, the nucleotide identification element sequence comprises a nucleotide sequence which is used to sequence the barcode polynucleotide and at least a portion of the multiple mRNA transcripts that are spliced to the barcode polynucleotide.

In some embodiments, in step i) the cell is within a population of cultured cells.

In some embodiments, in step i) the cell is obtained from or is present within an organism.

In some embodiments, the donor expression vector is delivered into the cell by a recombinant virus.

In some embodiments, the donor expression vector is delivered into the cell by transfection.

In some embodiments, the sequence of the barcode polynucleotide is from a high-diversity barcode library.

In some embodiments, the high-diversity barcode library is generated by shotgun cloning of polynucleotides.

In some embodiments, the sequence of the barcode polynucleotide is static.

In some embodiments, a recombinase may alter the sequence of the barcode polynucleotide.

In some embodiments, the recombinase is expressed in the cell into which the donor expression vector is delivered.

In some embodiments, the donor expression vector further comprises nucleotides in a sequence encoding the recombinase.

In some embodiments, a second expression vector comprising nucleotides in a sequence encoding the recombinase is delivered into the cell concurrently with the donor expression vector.

In some embodiments, the barcode polynucleotide comprises multiple unique DNA segments of multiple nucleotides separated by recombination sites, such that the multiple unique DNA segments are recombined by the recombinase when the recombinase is co-expressed with the donor expression vector in the cell.

In some embodiments, the barcode polynucleotide sequence comprises at least 2, 3, 4, 5, 6, 7, 8, 9, 10, 11, 12, 13, 14 or 15 unique DNA segments.

In some embodiments, each unique DNA segment comprises 1-200 nucleotides.

In some embodiments, the recombinase is Rci, and the recombination sites are each a pair of sfx recombination sites.

In some embodiments, the sfx recombination sites within each pair of sfx recombination sites are in an opposing orientation to each other.

In some embodiments, the recombinase is Cre, and the recombination sites are loxP sites.

In some embodiments, the recombinase is Flp, and the recombination sites are FRT sites.

In some embodiments, the recombinase is PhiC31 and the recombination sites are attB and attP sites.

Each embodiment disclosed herein is contemplated as being applicable to each of the other disclosed embodiments. Thus, all combinations of the various elements described herein are within the scope of the invention.

It is understood that where a parameter range is provided, all integers within that range, and tenths thereof, are also provided by the invention. For example, "0.2-5 mg/kg/day" is a disclosure of 0.2 mg/kg/day, 0.3 mg/kg/day, 0.4 mg/kg/day, 0.5 mg/kg/day, 0.6 mg/kg/day etc. up to 5.0 mg/kg/day.

Terms

Unless otherwise defined, all technical and scientific terms used herein have the same meaning as commonly understood by a person of ordinary skill in the art to which this invention belongs.

As used herein, and unless stated otherwise or required otherwise by context, each of the following terms shall have the definition set forth below.

As used herein, "about" in the context of a numerical value or range means±10% of the numerical value or range recited or claimed, unless the context requires a more limited range.

As used herein, the term "sequence" may mean either a strand or part of a strand of nucleotides, or the order of nucleotides within a strand or part of a strand, depending on the appropriate context in which the term is used. Unless specified otherwise in context, the order of nucleotides is recited from the 5' to the 3' direction of a strand.

The term "mRNA" refers to a nucleic acid transcribed from a gene from which a polypeptide is translated, and may include non-translated regions such as a 5'UTR and/or a 3'UTR. It will be understood that a trans-splicing ribozyme of the invention may comprise a nucleotide sequence that is complementary to any sequence of an mRNA molecule, including translated regions, the 5'UTR, the 3'UTR, and sequences that include both a translated region and a portion of either 5'UTR or 3'UTR.

"Operably linked" means that the coding sequence is linked to a regulatory sequence in a manner which allows expression of the coding sequence. Regulatory sequences include promoters, enhancers, and other expression control elements that are art-recognized and are selected to direct expression of the coding sequence.

A "transduced cell" is one that has been genetically modified. Genetic modification can be stable or transient. Methods of transduction (i.e., introducing vectors or constructs into cells) include, but are not limited to, liposome fusion (transposomes), viral infection, and routine nucleic acid transfection methods such as electroporation, calcium phosphate precipitation and microinjection. Successful transduction will have an intended effect in the transduced cell, such as gene expression, gene silencing, enhancing a gene target, or triggering target physiological event.

"Vector" refers to a vehicle for introducing a nucleic acid into a cell. Vectors include, but are not limited to, plasmids, phagemids, viruses, bacteria, and vehicles derived from viral or bacterial sources (Dassie et al., Nature Biotechnology 27, 839-846 (2009), Zhou and Rossi, Silence, 1:4 (2010), McNamera et al., Nature Biotechnology 24, 1005-1015 (2006)).

A "plasmid" is a circular, double-stranded DNA molecule. A useful type of vector for use in the present invention is a viral vector, wherein heterologous DNA sequences are inserted into a viral genome that can be modified to delete one or more viral genes or parts thereof. Certain vectors are capable of autonomous replication in a host cell (e.g., vectors having an origin of replication that functions in the host cell). Other vectors can be stably integrated into the genome of a host cell, and are thereby replicated along with the host genome.

Trans-Splicing Transcriptome Donors

Trans-splicing transcriptome donors of the present invention may comprise the Adeno Virus immediate early intron followed by a 3' splice site (CAG). However a person having ordinary skill in the art will understand that virtually any intron will be useful as part of a trans-splicing transcriptome donor in embodiments of the invention. Trans-splicing transcriptome donors may comprise introns that have a 3' splice site and an intron consensus sequence. The intron consensus sequence in IUPAC notation is:

Branch Point Consensus sequence: C-U-R-[A]-Y
  Must include an 'A' nucleotide
  Located 20-50 nucleotides upstream of the splice site
Polypyrimidine tract
C-A-G-[cut]-G splice site.

Non-limiting examples of introns that may be useful as part of trans-splicing transcriptome donors of the present invention are described in Alberts, Bruce (2008). Molecular biology of the cell. New York: Garland Science; Stryer, Lubert, Berg, Jeremy Mark, Tymoczko, John L. (2007). Biochemistry. San Francisco: W.H. Freeman; Kinniburgh et al. (July 1978). "The precursor of mouse β-globin messenger RNA contains two intervening RNA sequences". Cell 14 (3): 681-693; Chow et al. (September 1977). "An amazing sequence arrangement at the 5 ends of adenovirus 2 messenger RNA". Cell 12 (1): 1-8; Berget et al. (August 1977). "Spliced segments at the 5' terminus of adenovirus 2 late mRNA". Proc. Natl. Acad. Sci. U.S.A. 74 (8): 3171-5; Gilbert, Walter (1978). "Why genes in pieces". Nature 271 (5645): 501-501; Tajich et al. (2007). "Comparative genomic analysis of fungal genomes reveals intron-rich ancestors". Genome Biol. 8 (10): R223; Copertino D W, Hallick R B (December 1993). "Group II and group III introns of twintrons: potential relationships with nuclear pre-mRNA introns". Trends Biochem. Sci. 18 (12): 467-71; Padgett et al. (1986). "Splicing of messenger RNA precursors". Annu. Rev. Biochem. 55: 1119-50; Guthrie C, Patterson B (1988), "Spliceosomal snRNAs". Annu. Rev. Genet. 22: 387-419; Cech T R (1990). "Self-splicing of group I introns". Annu. Rev. Biochem. 59: 543-68; Michel F, Ferat J L (1995). "Structure and activities of group II introns". Annu. Rev. Biochem. 64: 435-61; Greer et al. (February 1983). "Mechanism of action of a yeast RNA ligase in tRNA splicing". Cell 32 (2): 537-46; Reinhold-Hurek B, Shub D A (May 1992). "Self-splicing introns in tRNA genes of widely divergent bacteria". Nature 357 (6374): 173-6; Rearick et al. (March 2011). "Critical association of ncRNA with introns". Nucleic Acids Res. 39 (6): 2357-66; Lambowitz A M, Belfort M (1993). "Introns as mobile genetic elements". Annu. Rev. Biochem. 62: 587-622; Penny et al. (November 2009). "An overview of the introns-first theory". Journal of Molecular Evolution 69 (5): 527-40; Rodriguez-Trelles et al. (2006). "Origins and evolution of spliceosomal introns". Annu. Rev. Genet. 40: 47-76; Mourier T, Jeffares D C (May 2003). "Eukaryotic intron loss". Science 300 (5624): 1393-1393; Roy S W, Gilbert W (March 2006). "The evolution of spliceosomal introns: patterns, puzzles and progress". Nature Reviews Genetics 7 (3): 211-21; de Souza S J (July 2003). "The emergence of a synthetic theory of intron evolution". Genetics 118 (2-3): 117-21; Lynch M (April 2002). "Intron evolution as a population-genetic process". Proceedings of the National Academy of Sciences 99 (9): 6118-23; Jeffares et al. (January 2006). "The biology of intron gain and loss". Trends in Genetics 22 (1): 16-22; Jeffares D C, Penkett C J, Bahler J (August 2008). "Rapidly regulated genes are intron poor". Trends in Genetics 24 (8): 375-8; and Castillo-Davis C I, Mekhedov S L, Hartl D L, Koonin E V, Kondrashov F A (August 2002). "Selection for short introns in highly expressed genes". Nature Genetics 31 (4): 415-8, the entire contents of each of which are hereby incorporated by reference.

Vectors

In certain embodiments, expression vectors encoding a trans-splicing transcriptome donor may be based on CMV-based or MSCV-based vector backbones. In certain embodiments, expression vectors may be based on self-inactivating lentivirus (SIN) vector backbones. Non-limiting examples of vector backbones and methodologies for construction of expression vectors suitable for use in connection with the subject application, and methods for introducing such expression vectors into various mammalian cells are found in the following references: Premsrurit P K. et al., *Cell*, 145(1):145-158, 2011, Gottwein E. and Cullen B. *Meth. Enzymol.* 427:229-243, 2007, Dickens et al., *Nature Genetics,* 39:914-921, 2007, Chen et al., *Science* 303: 83-86, 2004; Zeng and Cullen, *RNA* 9: 112-123, 2003, the contents of which are specifically incorporated herein by reference.

The vectors described in International application no. PCT/US2008/081193 (WO 09/055,724) and methods of making and using the vectors are incorporated herein by reference. The disclosure provided therein illustrates the general principles of vector construction and expression of sequences from vector constructs, and is not meant to limit the present invention.

Trans-splicing transcriptome donors can be expressed from vectors in almost any cell type. In a certain embodiment, the vector is a viral vector. Exemplary viral vectors include retroviral, including lentiviral, adenoviral, baculoviral and avian viral vectors.

Retroviruses from which the retroviral plasmid vectors can be derived include, but are not limited to, Moloney Murine Leukemia Virus, spleen necrosis virus, Rous sarcoma Virus, Harvey Sarcoma Virus, avian leukosis virus, gibbon ape leukemia virus, human immunodeficiency virus, Myeloproliferative Sarcoma Virus, and mammary tumor virus. A retroviral plasmid vector can be employed to transduce packaging cell lines to form producer cell lines. Examples of packaging cells which can be transfected include, but are not limited to, the PE501, PA317, R-2, R-AM, PA12, T19-14x, VT-19-17-H2, RCRE, RCRIP, GP+E-86, GP+envAm12, and DAN cell lines as described in Miller, *Human Gene Therapy* 1:5-14 (1990), which is incorporated herein by reference in its entirety. The vector can transduce the packaging cells through any means known in the art. A producer cell line generates infectious retroviral vector particles which include polynucleotide encoding a DNA replication protein. Such retroviral vector particles then can be employed, to transduce eukaryotic cells, either in vitro or in vivo. The transduced eukaryotic cells will express a DNA replication protein.

In certain embodiments, cells can be engineered using an adeno-associated virus (AAV). AAVs are naturally occurring defective viruses that require helper viruses to produce infectious particles (Muzyczka, N., *Curr. Topics in Microbiol. Immunol.* 158:97 (1992)). It is also one of the few viruses that can integrate its DNA into nondividing cells. Vectors containing as little as 300 base pairs of AAV can be packaged and can integrate, but space for exogenous DNA is limited to about 4.5 kb. Methods for producing and using such AAVs are known in the art. See, for example, U.S. Pat. Nos. 5,139,941, 5,173,414, 5,354,678, 5,436,146, 5,474,935, 5,478,745, and 5,589,377. For example, an AAV vector can include all the sequences necessary for DNA replication, encapsidation, and host-cell integration. The recombinant AAV vector can be transfected into packaging cells which are infected with a helper virus, using any standard technique, including lipofection, electroporation, calcium phosphate precipitation, etc. Appropriate helper viruses include adenoviruses, cytomegaloviruses, vaccinia viruses, or herpes viruses. Once the packaging cells are transfected and infected, they will produce infectious AAV viral particles which contain the polynucleotide construct. These viral particles are then used to transduce eukaryotic cells.

In certain embodiments, cells can be engineered using a lentivirus and lentivirus based vectors. Such an approach is advantageous in that it allows for tissue-specific expression in animals through use of cell type-specific pol II promoters, efficient transduction of a broad range of cell types, including nondividing cells and cells that are hard to infect by retroviruses, and inducible and reversible gene knockdown by use of tet-responsive and other inducible promoters. Efficient production of replication-incompetent recombinant lentivirus may be achieved, for example, by co-transfection of expression vectors and packaging plasmids using commercially available packaging cell lines, such as TLA-HEK293™, and packaging plasmids, available from Thermo Scientific/Open Biosystems, Huntsville, Ala.

Essentially any method for introducing a nucleic acid construct into cells can be employed. Physical methods of introducing nucleic acids include injection of a solution containing the construct, bombardment by particles covered by the construct, soaking a cell, tissue sample or organism in a solution of the nucleic acid, or electroporation of cell membranes in the presence of the construct. A viral construct packaged into a viral particle can be used to accomplish both efficient introduction of an expression construct into the cell and transcription of the encoded trans-splicing transcriptome donor. Other methods known in the art for introducing nucleic acids to cells can be used, such as lipid-mediated carrier transport, chemical mediated transport, such as calcium phosphate, and the like.

Examples of useful promoters in the context of the invention are tetracycline-inducible promoters (including TRE-tight), IPTG-inducible promoters, tetracycline transactivator systems, and reverse tetracycline transactivator (rtTA) systems. Constitutive promoters can also be used, as can cell- or tissue-specific promoters. Many promoters will be ubiquitous, such that they are expressed in all cell and tissue types. A certain embodiment uses tetracycline-responsive promoters, one of the most effective conditional gene expression systems in in vitro and in vivo studies.

Expression vectors of the present invention may contain regulatory sequences such as transcription control sequences, translation control sequences, origins of replication, and other regulatory sequences are compatible with the recombinant cell and that control the expression of nucleic acid molecules of the present invention. In particular, recombinant molecules of the present invention include transcription control sequences. Transcription control sequences are sequences which control the initiation, elongation and termination of transcription. Particularly important transcription control sequences are those which control transcription initiation, such as promoter, enhancer, operator and repressor sequences.

Genetic Barcodes

In some embodiments, expression vectors comprise a trans-splicing barcode cassette with a barcode nucleotide sequence that is altered within cells expressing the trans-splicing barcode cassette. In some embodiments, the barcode nucleotide sequence is altered by a recombinase. A non-limiting example of such a recombinase is Rci. Rci (recombinase for clustered inversion) is a site-specific recombinase (SSR) of the integrase (Int) family encoded by several incompatibility group 1 (Inc1) plasmids (Komano et al., 1999, Woodford et al., 2009). Rci recognizes 31 bp sfx sites of which there are many flavors. Sfx sites are composed of a conserved 7 bp core (determines direction), a conserved 12 bp right arm sequence, and a 12 bp variable sequence left arm. Rci is responsible for selecting one of the seven variable C-termini of the pilV gene of the R64 shufflon thus determining recipient specificity in liquid mating (Komano et al., 1999). Rci acts on artificial shufflons designed to have N orthogonal sequence fragments, each flanked by sfx sites. Moreover, Rci functions efficiently in mammalian cells in a similar fashion to other SSRs of the Int family, namely Cre and FLP.

Design of Barcode Cassette

Figure 3:
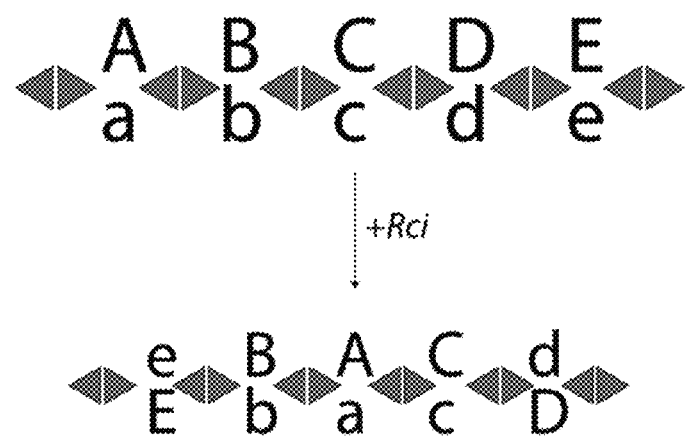
FIG. 3. Design of the Rci cassette. N barcode fragments (5 shown) are separated by pairs of sfx sites. Upon exposure to Rci, the cassette is shuffled.
Figure 4:
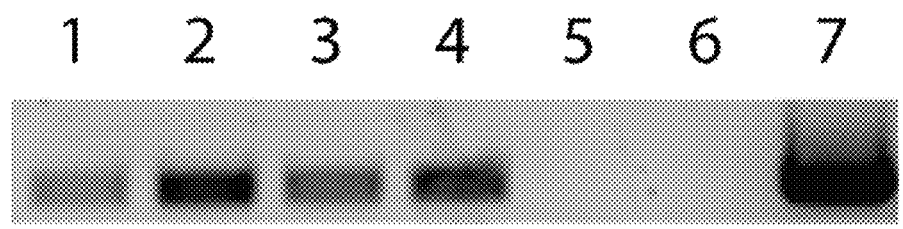
FIG. 4. HEK293 cells harboring a genomic substrate were transfected with eGFP-Rci (1); Rci (2); eGFP-NLS-Rci (3); NLS-Rci (4); sham (5); Rci in non-substrate-cell (6); positive control from-plasmid (7).

A schematic view of a non-limiting and exemplary barcode cassette is shown in FIG. 3. Briefly, N unique DNA segments of 100 base pairs (bp) each are separated by pairs of sfx sites in opposing orientation. This configuration allows the maximal configurations of each barcode segment—every segment can appear in any position along the cassette and in either its original or reverse complement orientation. Thus the total cassette diversity is the product of the possible orientation of all of the fragments (2n) and the permutations of the order of the fragments within the cassette (n!) is represented by the formula $2^n n!$, where n is the number of fragments in the cassette. Because of the small input space (i.e. <10 fragments) it is possible to accurately reconstruct barcode identities even in the case of high sequencing error rates.

All publications and other references mentioned herein are incorporated by reference in their entirety, as if each individual publication or reference were specifically and individually indicated to be incorporated by reference. Publications and references cited herein are not admitted to be prior art.

This invention will be better understood by reference to the Experimental Details which follow, but those skilled in the art will readily appreciate that the specific experiments detailed are only illustrative of the invention as defined in the claims which follow thereafter.

EXPERIMENTAL DETAILS

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only.

Example 1: Trans-Splicing Transcriptome Profiling

First, whether the cellular tagging indeed happens in vivo and not as a result of template switching during RT-PCR was tested. HEK293 cells were separately co-transfected with splicing BC1 and GFP (with an intron) or splicing BC2 and mouse SST (with an intron) and harvested cells 48 hours after transfection.

The splicing donor consists of the Adeno Virus immediate early intron followed by a 3' splice site (CAG), although it is expected that any intron will work for this purpose. The sequence of the intron is given below. Immediately following the 3' splice site is a unique barcode sequence. This barcode sequence can be a static single barcode, or can consist of a high-diversity barcode library generated by a variety of means including but not limited to shotgun cloning of oligonucleotides, in vivo barcode generation by a recombinase, etc. Following the barcode, additional known sequence elements are present to aid in reverse transcription, and high-throughput sequencing preparations.
Adeno Virus IE Intron:

(SEQ ID NO: 1)
GGCCTACTTATCCTGTCCCTTTTTTTTCCACAG

Figure 2:
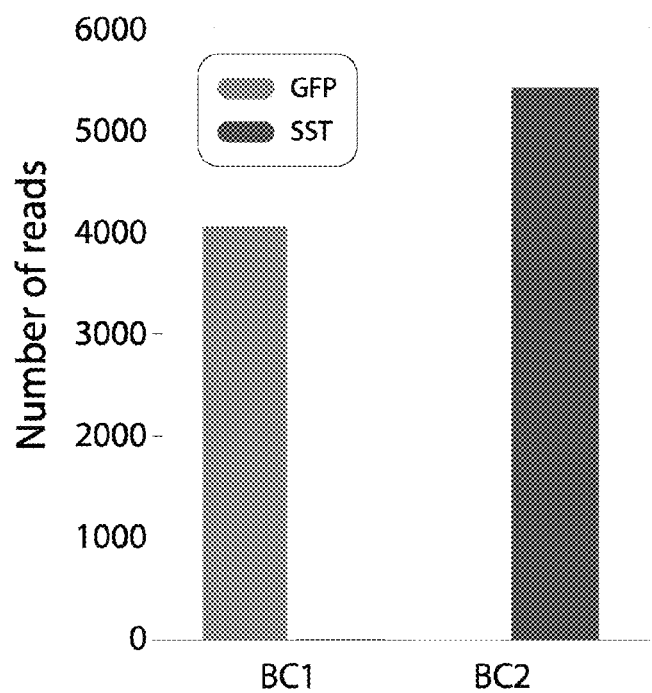
FIG. 2. BC1 and BC2 are found almost exclusively with their co-transfected partner (GFP or SST, respectively) proving that transcript tagging occurs in vivo.

The cells were mixed together to emulate a heterogenous population and RNA was then Trizol extracted, reverse transcribed into cDNA, and PCR amplified adding adapters for Illumine high-throughput sequencing. Many instances of GFP transcript tagged with BC1 and SST tagged with BC2 were expected to be found, but not the opposite (GFP tagged with BC2 or SST tagged with BC1). Using bowtie2 reads were mapped to GFP and SST and found that 4046 reads of BC1 aligned to GFP, while only 10 reads aligned to SST (as expected). For BC2 5170 reads were found to map to SST and only 3 reads to GFP. This data is summarized in FIG. 2. Additional analysis showed that there was a high correspondence between cellular transcripts tagged in BC1 and BC2 and, encouragingly, that among the most abundant transcripts were some that were cell-type specific (Table 1).

TABLE 1

List of top hits and their read count from BC2 library. Note the top hit, SST which was co-transfected with BC2 and the second hit, KLF15, which is a kidney specific gene.

| Gene ID | # Reads |
| --- | --- |
| SST | 9353 |
| KLF15 | 2668 |
| HBB | 998 |
| SSBP2 | 480 |
| SEP15 | 424 |
| TRIM4 | 420 |
| SMPD4 | 420 |
| HNRNPA2B1 | 340 |
| RANBP6 | 322 |
| PODXL2 | 315 |

To compare the method with traditional RNA-seq methods, RNA seq libraries were prepared using polyA RT instead of using the specific primer that was used to extract spliced sequences.

Example 2: Genetic Barcode Cassettes

Rci Operation in Bacterial Cells

A plasmid containing the Rci gene under an inducible T7 promoter and a barcode cassette consisting of 5 fragments was transformed into BL21-DE3 (NEB). Cells were grown in Overnight Express Media (Calbiochem) for induction of the Rci protein. After growth, cells were plated for clonal analysis. Twenty colonies were chosen for each condition (+ and − Rci induction) and analyzed by Sanger sequencing. All 20 colonies without Rci expression show no recombination. However, when Rci was induced, recombination events are detected in 8/20 colonies and the barcode cassette shuffles (Table 2).

TABLE 2

Rci recombination in bacteria

| BC fragment sequence | | | | | Likely recombination event |
| --- | --- | --- | --- | --- | --- |
| −5 | −4 | −3 | −2 | −1 | sfx101R + sfx101L |
| 1 | −2 | 3 | 4 | 5 | sfx102L + sfxb106R |
| 1 | 2 | 3 | −4 | 5 | sfxa112L + sfxa109R |
| 1 | 2 | −5 | −4 | −3 | sfxb106R + sfx101L |
| 1 | 2 | 3 | −4 | 5 | sfxa112L + sfxa109R |
| 1 | 2 | 3 | −4 | 5 | sfxa112L + sfxa109R |
| −3 | −2 | −1 | 4 | 5 | sfx101R + sfxa112L |
| 1 | −4 | −3 | −2 | 5 | sfx102L + sfxa109R |

Rci Operation in Mammalian Cells

To test if the use of Rci in mammalian cells was feasible, an experiment was set up in which inversion of a genomic DNA sequence could be detected by polymerase chain reaction (PCR). Various Rci constructs were transfected into HEK293 cells harboring a genomic substrate. PCR shows that Rci can function in mammalian cells, on genomic DNA.

Example 3. Rci Barcoding in Bacterial Cells

Figure 5A:
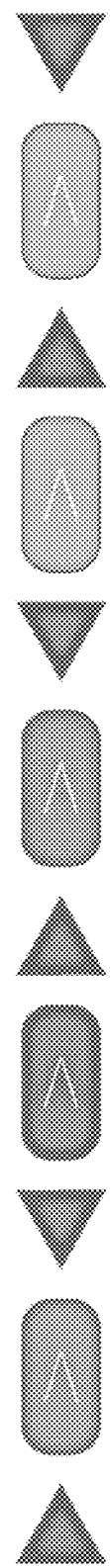
FIG. 5. Barcode shuffling in bacterial cells. A five-fragment barcode cassette (A) was synthesized and cloned into a plasmid containing the Rci coding sequence. The barcode was stable in bacterial cells as evidenced by the lack of shuffling without Rci expression (B). Rci expression from the induced lac promoter caused modest levels of recombination (C). Constitutive expression of Rci from the medium-strength kanamycin promoter resulted in extensive shuffling of the barcode cassette (D). In (B, C, D) > and < indicate the orientation of the respective fragments. To the right of each graph, unique sequences are numbered (- indicates the original sequence).
Figure 5B:
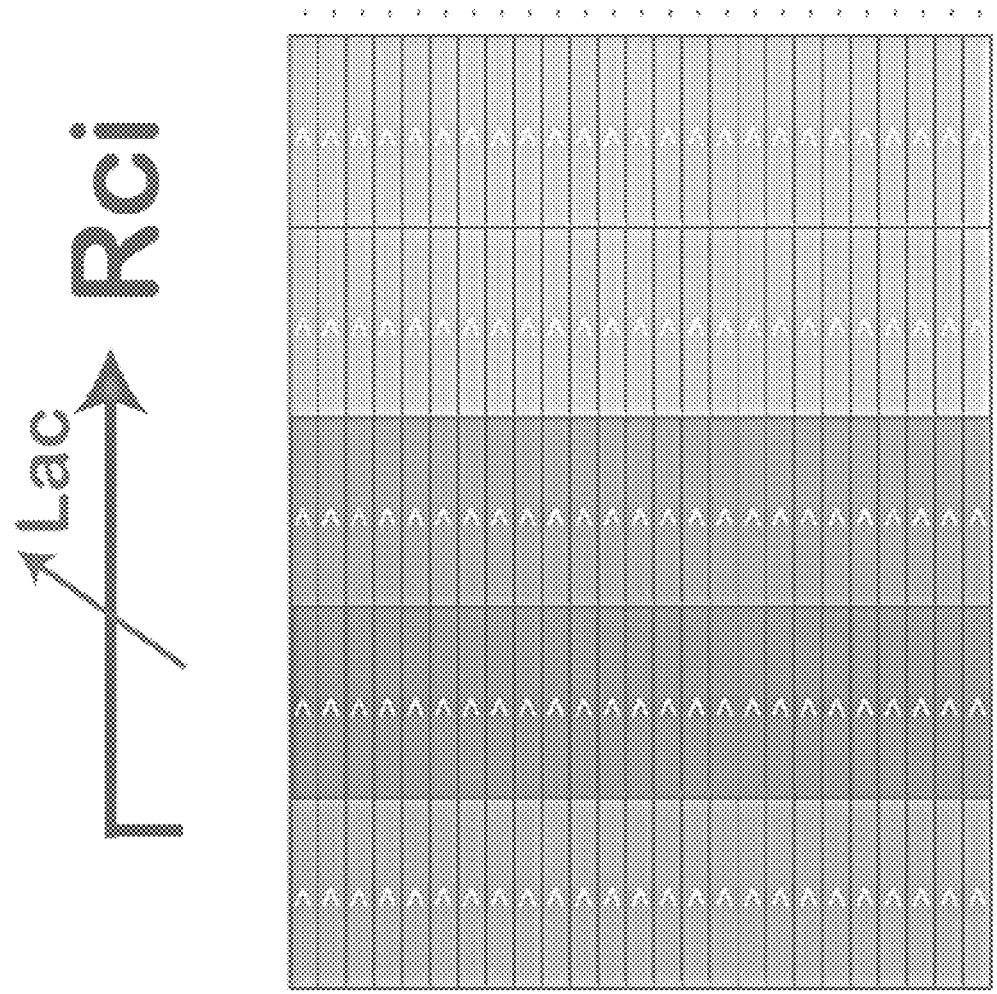
Figure 5C:
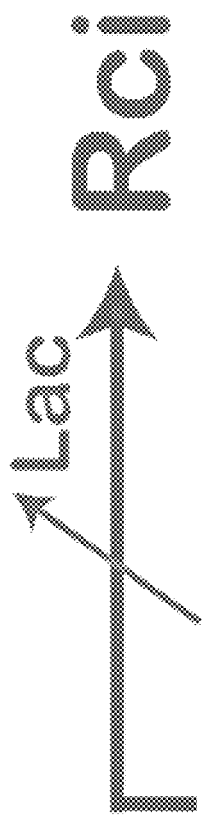
Figure 5C:
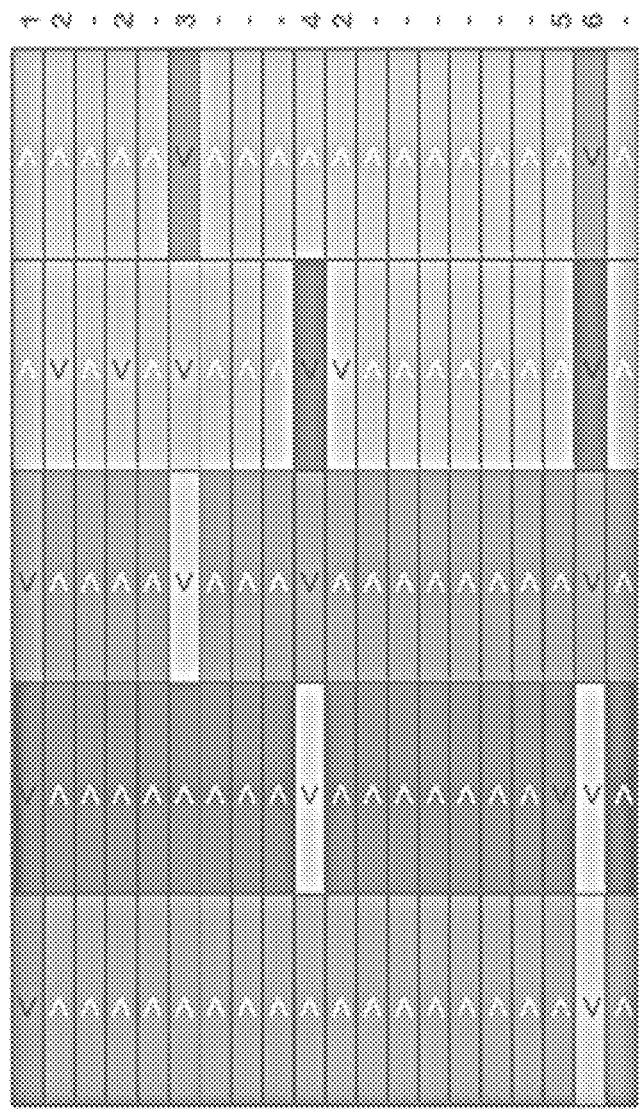
Figure 5D:
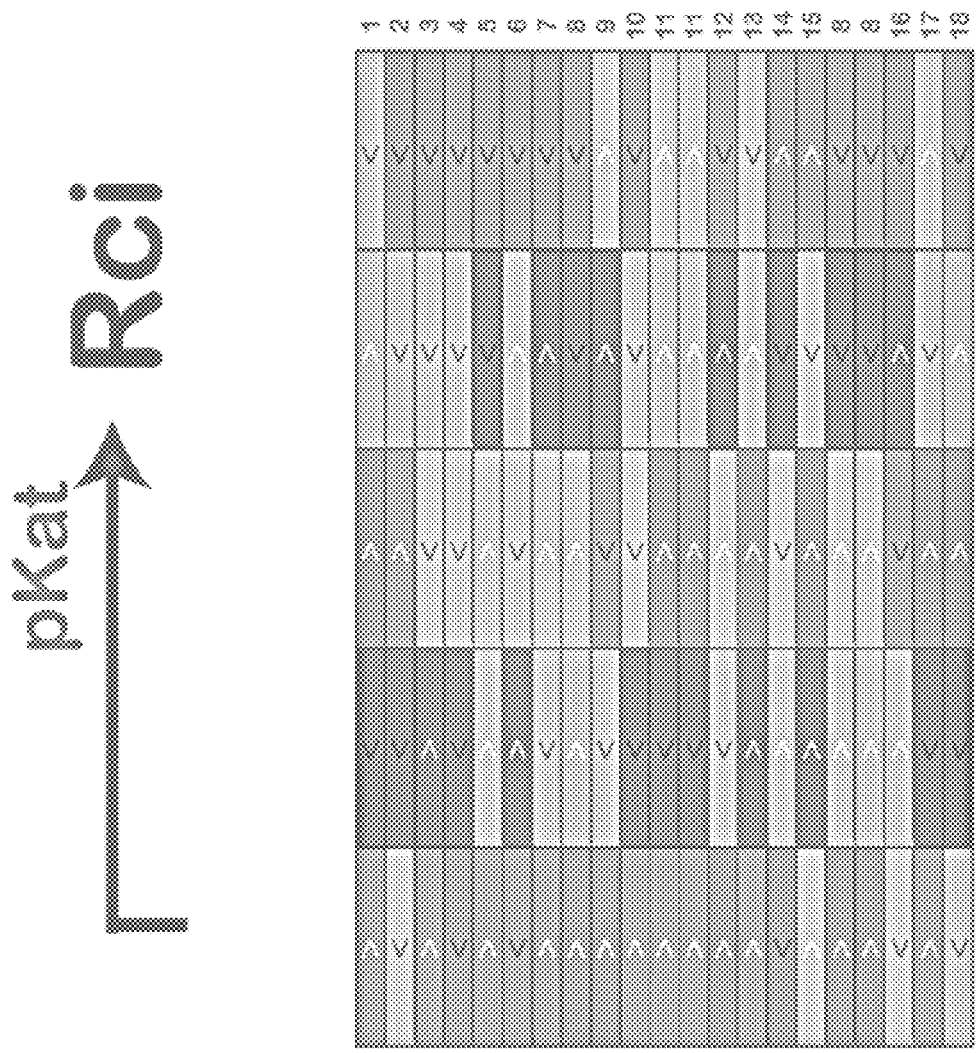

In order to test a basic Rci barcoding scheme, a 5-fragment barcode cassette was synthesized (FIG. 5A) and cloned into a low copy plasmid containing the Rci gene under the control of a lac inducible promoter. This ensures that all barcodes that are transformed into cells are exposed to the Rci protein. Bacterial cells were transformed with the plasmid and allowed to grow for 16 hours with or without induction. After growth, cells were plated for clonal analysis. Twenty-five colonies were chosen for each condition and assayed by Sanger sequencing. Sequence reads were analyzed with our alignment algorithm in order to automatically reconstruct full barcodes. Reads that could not be fully reconstructed from sequencing data were discarded from further analysis. No recombination (0/25) was observed in the absence of Rci induction (FIG. 5B). In contrast, a modest rate of recombination was found after induction with 8/20 colonies shuffled (FIG. 5C). Surprisingly each sequence could be explained by a single recombination event. It was hypothesized herein that the low rate of recombination observed was due to the short window of protein expression and the high amplification of the un-shuffled (original) plasmid before exposure to any Rci protein. In addition, it was found that Rci driven by this inducible system was highly expressed but mostly insoluble. Therefore, experiments transitioned to a system in which a medium strength promoter (the kanamycin promoter, pKat) drove Rci expression at modest levels, constitutively. The experiments were repeated and all reconstructed sequences were found to have undergone recombination (FIG. 5D). Many of the shuffled cassettes could only be explained by multiple recombination events, and interestingly, recombination events were found between many different pairs of sfx sites. Moreover, 18/21 colonies were unique. Because the potential diversity of this cassette design is low (theoretical diversity=384), the repeats are in line with expectations based on collision counting.

Example 4. Barcoding of Mammalian Cells

Figure 6D:
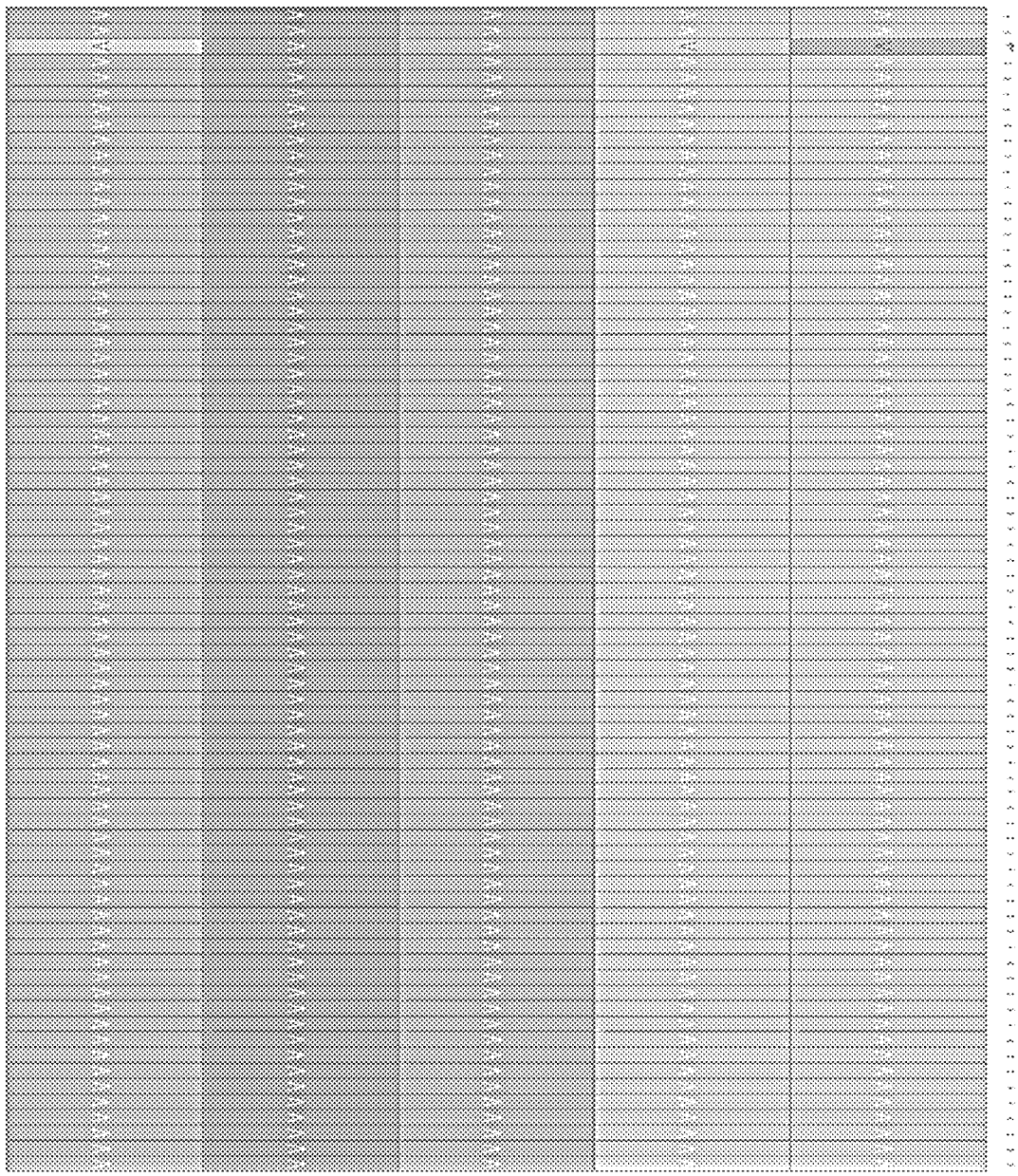
FIG. 6. Rci barcoding in mammalian cells. Rci traffics to the nucleus without the addition of exogenous nuclear localization signals (A). A sensitive PCR-based strategy was designed to detect inversion of a DNA segment (B). The inversion assay cassette was introduced into the genome of HEK293 cells, which were subsequently transfected with different variants of Rci. Rci can induce recombination in mammalian cells (C). Cells harboring an inversion cassette were transfected with: 1. eGFP::Rci. 2. Rci, 3. eGFP-NLS- Rci, 4. NLS-Rci, all of which induced recombination as assayed by PCR. Transfection of eGFP (5) did not induce recombination. Transfection of Rci into unmodified cells does not produce a PCR product (6). Low rates of recombination were observed (1/80 assayed)(D).

Though Rci barcoding is useful as a tool in bacteria, interests in the mammalian brain lead to testing the feasibility of RCI barcoding in mammalian systems. In order to barcode mammalian cells, a single copy of the barcode cassette should be present at a defined genomic locus. Rci, then, must make its way to the nucleus, bind genomic DNA, and mediate shuffling through several recombination events. First, whether the native form of Rci would traffic to the nucleus of mammalian cells was tested. Briefly, construct with GFP fused to the N-terminal of Rci (GFP::Rci) was tested. Transient transfection of GFP::Rci into HEK293 cells showed GFP::Rci confined to the nucleus (FIG. 6A). To test if Rci could mediate recombination on a genomic substrate, a sensitive inversion assay using the polymerase chain reaction (PCR) was developed. A primer binding site flanked by inverted repeats of sfx sites was cloned directly downstream of a primer binding site facing the same direction. Successful PCR amplification can only occur if the primers are in opposing orientation. Therefore, successful PCR was used as an assay for whether or not recombination occurs (FIG. 6B). This cassette was introduced into a HEK cells by use of an attP integration cell line (Calos). Different variants of Rci were then transiently transfected and assayed for recombination by PCR. Rci was found to function in mammalian cells (FIG. 6C). Interestingly, markedly reduced recombination was observed when protein domains were fused to the C-terminal of Rci.

Next, whether the entire Rci barcoding paradigm would work in mammalian cells by introducing a 5-fragment barcode cassette and Rci recombinase into the mammalian genome was tested. Unfortunately, this configuration proved toxic to the cells, perhaps because of formation of delicate chromosomal site. Instead, the cassette was introduced into the genome without the Rci coding sequence. These cells, mShuffle cells, were stable, propagated for many generations, and showed no recombination without addition of the Rci protein. Transient transfection of Rci was used to induce shuffling of the cassette. However, low rates of recombination were observed (1/80 assayed, FIG. 6D). Interestingly, this barcode was produced by multiple recombination events. Work is ongoing in our lab to optimize Rci efficiency in mammalian cells to adapt this system for neuronal barcoding.

Discussion

The present invention provides a novel method for tagging transcripts within individual cells of a heterogeneous population by hijacking the cellular splicing machinery.

Previously, researchers have attempted to use the spliceosome to splice RNA molecules in trans. This technique, known as Spliceosome Mediated RNA Trans-splicing (SMRT), has the potential to target individual RNA molecules with the purpose of repairing mutated transcripts and/or delivering targeted therapeutics (i.e. cytotoxins to kill cancerous cells). However, the technique is plagued by promiscuity of the splicing events. It has been shown that expression of an intron sequence followed by an exon causes trans-splicing to occur between the artificial exon and many cellular transcripts[1]. Herein, it was reasoned that, combined with cellular barcoding[2,3] this lack of specificity could be exploited to stochastically tag actively transcribed mRNA with the spliceosome. By replacing the 3' exon with a unique barcode, expression profiles of individual cells within a population can be identified by high-throughput sequencing (FIG. 1). Additional useful sequence elements can be added to aid in affinity purification. The splice donor barcode construct can be delivered by a variety of methods (transgenic, viral infection, etc.) and can be made dependent on trans-activators (i.e. Cre, ttA, Flp, PhiC31, etc) to achieve bulk transcriptomes from specific, genetically defined, populations of cells (i.e. Sst-Cre).

Genetic Barcodes

Heterogeneity is a ubiquitous feature of biological systems. A complete understanding of such systems thus requires a method to uniquely identify and track individual components and their interactions with each other. The present invention describes a method of uniquely tagging individual cells, and the transcripts of individual cells, with a genetic "barcode" that can be recovered with high-throughput sequencing. This method is useful in tracking cell fate decisions, interactions of cells within a network, and/or heterogeneity in expression profiles in complex biological samples including brain and cancer tissue samples, or even entire organisms.

For example, the application of this method in the mouse brain constitutes one of the core components of a broader effort to convert neural connectivity into a DNA sequencing problem. See, e.g., Zador et al. (2012) "Sequencing the connectome" PLoS Biol 10(10): e1001411, the entire contents of which are incorporated herein by reference.

Most current approaches to tagging individual cells with a genetic barcode rely on the creation of high-diversity retroviral vectors in vitro and subsequent infection of the viral library. This approach has proved useful in tagging neurons (Golden et al. 1995) and hematopoietic stem cells (Lu et al. 2011) for lineage analysis. However, retroviral infection is limited to a subset of organisms and is difficult to scale to whole organisms. Generation of barcodes in vivo ensures the labeling of all cells. Mechanisms for generating somatic diversity exist in the immune system—though a clever repurposing of VDJ recombination for in vivo cellular tagging yielded surprisingly low barcode diversity (Heigst et al.). Exogenous recombineses have been successfully used to generate diverse combinations of colors—by mediating recombination of an array of fluorophore coding sequences separated by recombination sites—for cellular tagging purposes (Livet, et al. 2007). Unfortunately, due to the limited number of incompatible recombination sites and the fact that excision dominates, this approach cannot be readily scaled to yield higher diversity.

The present invention provides a modular genetically encoded barcode system that is easily scalable, cross-platform (applicable across model organisms), compatible with high-throughput sequencing technologies, and robust to sequencing errors. Some embodiments of the invention combine an exogenous site-specific recombinase, Rci and a cassette of barcode fragments. As in the Brainbow system, exposure of the cassette to the recombinase leads to recombination, thus generating a unique label in each cell. However, unlike the recombinase, Cre, used in the Brainbow system, Rci can only mediate inversion events. Thus, the cassette is shuffled by inversion of the fragments alone and/or in groups. The potential diversity with this architecture is $2^n n!$, where n is the number of segments in the cassette. With only 12 unique segments, the diversity approaches 2 trillion—far more than enough to uniquely label every neuron in the mouse brain. Additional segments greatly increase the diversity making this a scalable approach. Moreover, because the input space is small (only 12 unique segments), each segment can be designed to be maximally orthogonal, thus rendering the barcode readout highly robust to DNA sequencing errors.

REFERENCES

1. Kikumori, T., Cote, G. J. & Gagel, R. F, Promiscuity of pre-mRNA spliceosome-mediated trans splicing: a problem for gene therapy? *Human gene therapy* 12, 1429-41 (2001).
2. Lu, R. Neff, N. F., Quake, S. R. & Weissman, I. L. Tracking single hematopoietic stem cells in vivo using high-throughput sequencing in conjunction with viral genetic barcoding. *Nature Biotechnology* 29, 928-933 (2011).
3. Golden, J. a, Fields-Berry, S. C. & Cepko, C. L. Construction and characterization of a highly complex retroviral library for lineage analysis. *Proceedings of the National Academy of Sciences of the United States of America* 92, 5704-8 (1995).
4. Heijst, J. W. J. V., Urbanus, J., Jacobs, H. & Schumacher, T. N. M. Chapter 7: Tracing cellular origins by inducible DNA diversification in vivo. Cancer available from open-access.leidenuniv.nl/bitstream/handle/1887/15721/Chapter%20 7.pdf?sequence=5
5. Livet, J. et al. Transgenic strategies for combinatorial expression of fluorescent proteins in the nervous system. *Nature* 450, 56-62 (2007).
6. Komano, T. SHUFFLONS: Multiple Inversion Systems and Integrons. Annual Review of Genetics 33, 171-191 (1999).
7. Woodford, N. et al. Complete Nucleotide Sequences of Plasmids pEK204, pEK499, and pEK516, Encoding CTX-M Enzymes in Three Major *Escherichia coli* Lineages from the United Kingdom, All Belonging to the International 025:H4-ST131 Clone. Antimicrob Agents Chemother 53, 4472-4482 (2009).

What is claimed is:

1. A method of identifying mRNA transcripts in the transcriptomes of multiple cells within a population of cells comprising
  i) delivering into each of at least two cells a donor expression vector comprising nucleotides in a sequence encoding a trans-splicing barcode cassette having the same nucleotide sequence, wherein the trans-splicing barcode cassette comprises
    a) a first portion, the nucleotide sequence of which encodes an intron comprising as part of its 3' end, or followed at its 3' end by a splice-site nucleotide sequence;
    followed at its 3' end by,
    b) a second portion, the nucleotide sequence of which encodes a barcode polynucleotide;
    followed at its 3' end by
    c) a third portion, which encodes a nucleotide identification element sequence,
    wherein the portion of the nucleotide sequence of the expression vector that encodes the barcode polynucleotide is altered within the at least two cells, such that each of the at least two cells within the population expresses copies of the trans-splicing barcode cassette having a unique barcode polynucleotide sequence,
  ii) exposing the cells to conditions such that each of the at least two cells produces multiple copies of the trans-splicing barcode cassette encoded by the donor expression vector, which multiple copies of the trans-splicing barcode cassette each splice the barcode polynucleotide onto a mRNA transcript of the at least two cells, thereby forming multiple spliced mRNA transcripts of the cell, each spliced to the barcode polynucleotide; and iii) identifying the multiple mRNA transcripts that are spliced to the barcode polynucleotides, thereby identifying mRNA transcripts in the transcriptomes of multiple cells within a population of cells.

2. The method of claim 1, wherein the intron comprises the Adeno Virus immediate early intron.

3. The method of claim 2, wherein the Adeno Virus immediate early intron is followed at its 3' end by the splice-site nucleotide sequence.

4. The method of claim 1, wherein the splice-site nucleotide sequence is CAG.

5. The method of claim 1, wherein the intron is other than the Adeno Virus immediate early intron.

6. The method of claim 1, wherein the population of cells is an in vitro culture of cells.

7. The method of claim 1, wherein the population of cells is within the tissue obtained from or present within an organism.

8. The method of claim 1, wherein a recombinase alters the nucleotide sequence of the expression vector that encodes the barcode nucleotide sequence.

9. The method of claim 8, wherein the recombinase is expressed in each cell into which a trans-splicing barcode cassette is delivered.

10. The method of claim 1, wherein the barcode polynucleotide comprises multiple unique DNA segments of multiple nucleotides separated by recombination sites, such that the multiple unique DNA segments are recombined by a recombinase when the recombinase is co-expressed with the donor expression vector in each of the at least two cells.

11. The method of claim 10, wherein the barcode polynucleotide sequence comprises at least 2, 3, 4, 5, 6, 7, 8, 9, 10, 11, 12, 13, 14 or 15 unique DNA segments.

12. The method of claim 11, wherein each unique DNA segment comprises 1-200 nucleotides.

13. The method of claim 10, wherein the recombinase is Rci, and the recombination sites are each a pair of sfx recombination sites.

14. The method of claim 13, wherein the sfx recombination sites within each pair of sfx recombination sites are in an opposing orientation to each other.

15. The method of claim 10, wherein the recombinase is Cre, and the recombination sites are loxP sites.

16. The method of claim 10, wherein the recombinase is Flp, and the recombination sites are FRT sites.

17. The method of claim 10, wherein the recombinase is PhiC31, and the recombination sites are att sites.

18. The method of claim 1,
wherein in step iii) the nucleotide identification element sequence is used to identify the multiple mRNA transcripts that are spliced to the barcode polynucleotide; or
wherein the nucleotide identification element sequence comprises a nucleotide sequence which is used to
a) identify the multiple mRNA transcripts that are spliced to the barcode polynucleotides,
b) reverse transcribe the barcode polynucleotide and at least a portion of the multiple mRNA transcripts that are spliced to the barcode polynucleotide, and/or
c) sequence the barcode polynucleotide and at least a portion of the multiple mRNA transcripts that are spliced to the barcode polynucleotide.

19. The method of claim 1, wherein each donor expression vector further comprises nucleotides in a sequence encoding the recombinase, or wherein a second expression vector comprising nucleotides in a sequence encoding the recombinase is delivered into the at least two cells concurrently with the donor expression vector.

20. A method of identifying mRNA transcripts in the transcriptome of a cell comprising
i) delivering into the cell a donor expression vector comprising nucleotides in a sequence encoding a trans-splicing barcode cassette, wherein the trans-splicing barcode cassette comprises
a) a first portion, the nucleotide sequence of which encodes an intron comprising as part of its 3' end, or followed at its 3' end by a splice-site nucleotide sequence;
followed at its 3' end by,
b) a second portion, the nucleotide sequence of which encodes a barcode polynucleotide, which is alterable by a recombinase;
followed at its 3' end by
c) a third portion, which encodes a nucleotide identification element sequence,
wherein a recombinase alters the nucleotide sequence of the expression vector that encodes the barcode nucleotide sequence,
ii) exposing the cell to conditions such that the cell produces multiple copies of the trans-splicing barcode cassette encoded by the donor expression vector, which multiple copies of the trans-splicing barcode cassette each splice the barcode polynucleotide onto a mRNA transcript of the cell, thereby forming multiple mRNA transcripts of the cell, each spliced to the barcode polynucleotide; and
iii) identifying the multiple mRNA transcripts that are spliced to the barcode polynucleotides, thereby identifying mRNA transcripts in the transcriptome of the cell.

21. The method of claim 20,
wherein in step iii) the nucleotide identification element sequence is used to identify the multiple mRNA transcripts that are spliced to the barcode polynucleotide; or
wherein the nucleotide identification element sequence comprises a nucleotide sequence which is used to
a) identify the multiple mRNA transcripts that are spliced to the barcode polynucleotide,
b) reverse transcribe the barcode polynucleotide and at least a portion of the multiple mRNA transcripts that are spliced to the barcode polynucleotide, and/or
c) sequence the barcode polynucleotide and at least a portion of the multiple mRNA transcripts that are spliced to the barcode polynucleotide.

22. The method of claim 20,
a) wherein the recombinase is expressed in the cell into which the donor expression vector is delivered;
b) wherein the donor expression vector further comprises nucleotides in a sequence encoding the recombinase; or
c) wherein a second expression vector comprising nucleotides in a sequence encoding the recombinase is delivered into the cell concurrently with the donor expression vector.

23. The method of claim 20, wherein the barcode polynucleotide comprises multiple unique DNA segments of multiple nucleotides separated by recombination sites, such that the multiple unique DNA segments are recombined by the recombinase when the recombinase is co-expressed with the donor expression vector in the cell.

24. The method of claim 23,
a) wherein the recombinase is Rci, and the recombination sites are each a pair of sfx recombination sites;
b) wherein the recombinase is Rci, and the recombination sites are each a pair of sfx recombination sites, and wherein the sfx recombination sites within each pair of sfx recombination sites are in an opposing orientation to each other;
c) wherein the recombinase is Cre, and the recombination sites are loxP sites;
d) wherein the recombinase is Flp, and the recombination sites are FRT sites; or
e) wherein the recombinase is PhiC31, and the recombination sites are attB and attP sites.

* * * * *

SEQUENCE LISTING

<160> NUMBER OF SEQ ID NOS: 1

<210> SEQ ID NO 1
<211> LENGTH: 33
<212> TYPE: DNA
<213> ORGANISM: Adenovirus

<400> SEQUENCE: 1
ggcctactta tcctgtccct tttttttcca cag          33